United States Patent [19]

Andrew et al.

[11] Patent Number: 5,627,869
[45] Date of Patent: May 6, 1997

[54] MAMMOGRAPHY APPARATUS WITH PROPORTIONAL COLLIMATION

[75] Inventors: Ted M. Andrew, New Milford, Conn.; Kenneth F. Defreitas, Patterson, N.Y.; Samson L. Pennatto, Danbury; James A. Princehorn, Newtown, both of Conn.

[73] Assignee: ThermoTrex Corporation, San Diego, Calif.

[21] Appl. No.: 562,115

[22] Filed: Nov. 22, 1995

[51] Int. Cl.⁶ ........................................ H05G 1/30
[52] U.S. Cl. ........................................ 378/37; 378/150
[58] Field of Search .................... 378/37, 150, 151, 378/152, 153

[56] References Cited

U.S. PATENT DOCUMENTS

| | | | |
|---|---|---|---|
| Re. 33,634 | 7/1991 | Yanaki | 378/110 |
| 3,502,878 | 3/1970 | Stewart et al. | 378/151 |
| 3,991,316 | 11/1976 | Schmidt et al. | 378/37 |
| 4,744,099 | 5/1988 | Huettenrauch et al. | 378/37 X |
| 4,890,311 | 12/1989 | Saffer | 378/37 |
| 4,930,143 | 5/1990 | Lundgren et al. | 378/37 |
| 4,947,417 | 8/1990 | Hartwell | 378/147 |
| 4,998,270 | 3/1991 | Scheid et al. | 378/155 |
| 5,018,176 | 5/1991 | Romeas et al. | 378/37 |
| 5,335,257 | 8/1994 | Stunberg | 378/37 |

FOREIGN PATENT DOCUMENTS 4009145  1/1992  Japan ........................ 378/37

Primary Examiner—David P. Porta
Attorney, Agent, or Firm—Ware, Fressola, Van Der Sluys & Adolphson LLP

[57] ABSTRACT

A mammography apparatus for obtaining mammography images with optimal beam collimation is disclosed. Proportional control of collimator element position based upon compression paddle position and dimension inputs is provided to obtain optimal collimation of the X-ray beam for a desired imaging technique and compressed breast thickness.

7 Claims, 5 Drawing Sheets

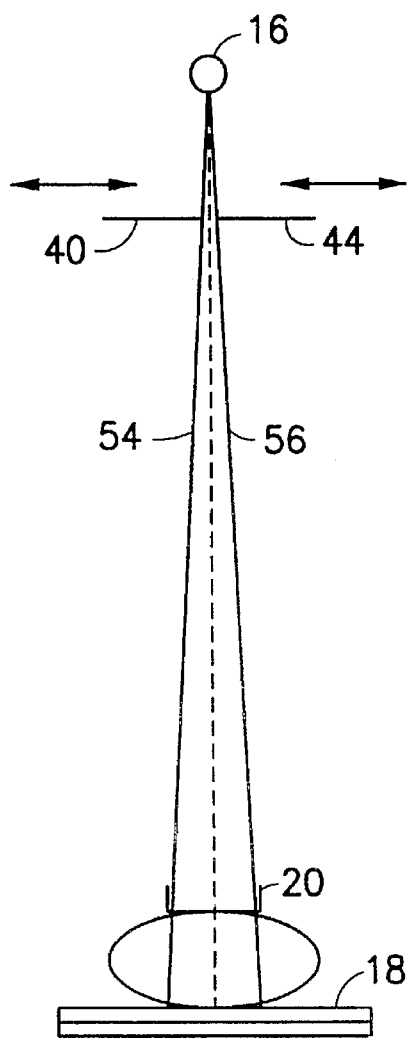
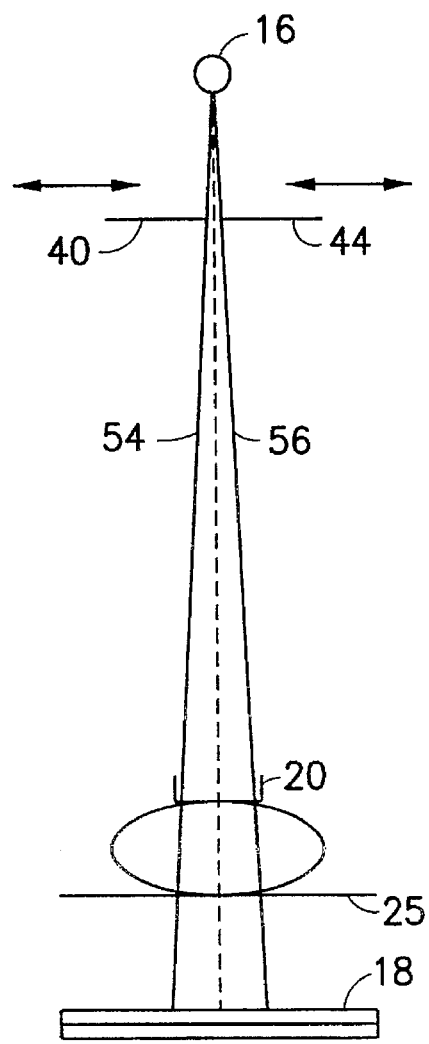
FIG. 5A　　　　　　　　FIG. 6A
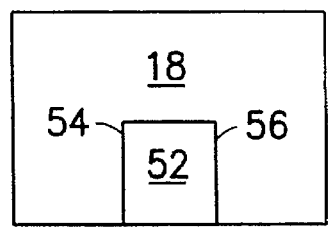
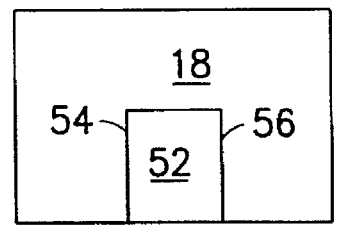
FIG. 5B　　　　　　　　FIG. 6B

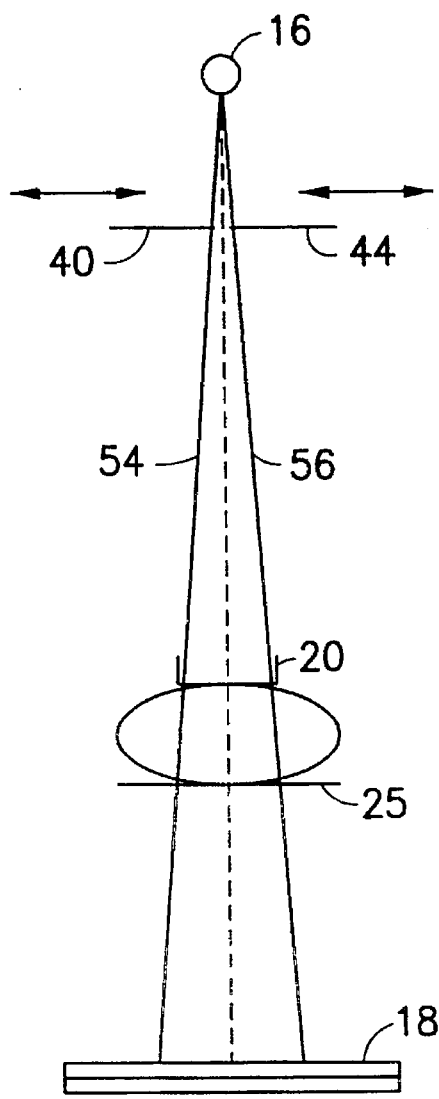
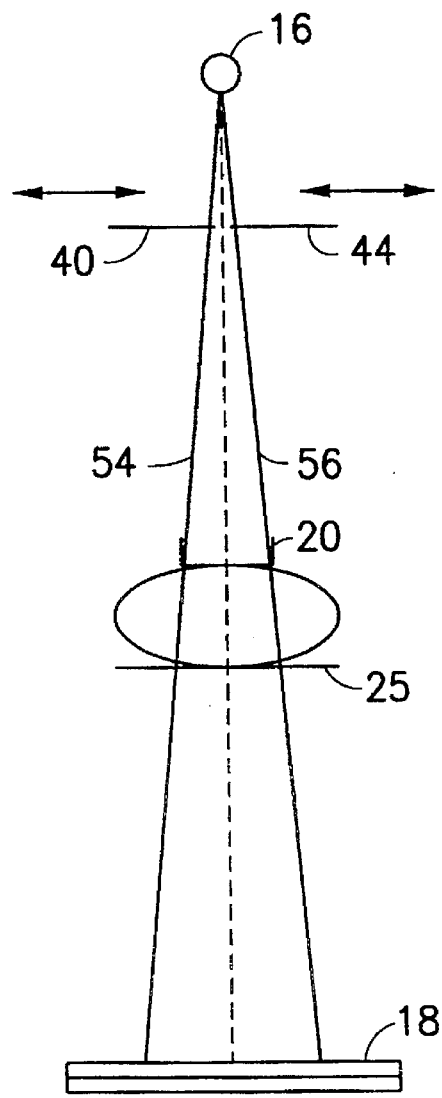
FIG. 7A  FIG. 8A
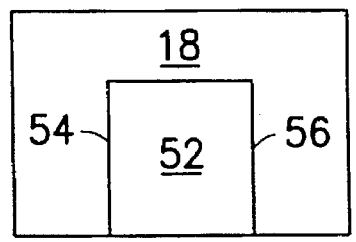
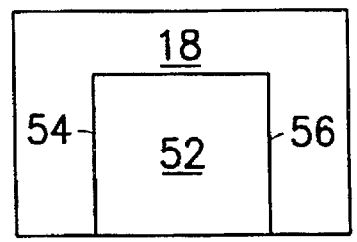
FIG. 7B  FIG. 8B

MAMMOGRAPHY APPARATUS WITH PROPORTIONAL COLLIMATION

BACKGROUND OF THE INVENTION

1. Field of the Invention

The present invention generally relates to a medical X-ray imaging. More particularly, the present invention relates to a mammography apparatus wherein the tube collimator is adjusted automatically to provide a collimated X-ray beam that is appropriate for the dimension and position of a compression paddle to reduce the potential for scattered X-rays that may interfere with image quality.

2. Description of the Prior Art

As is well understood by those skilled in the art, sharp contrast and high resolution images are highly desirable in virtually all X-ray imaging applications. In medical X-ray imaging, sharp contrast and high resolution images are necessary to enable as accurate medical diagnosis as possible. As compared with some other medical X-ray imaging, such as the imaging of skeletal structures, mammography demands very sharp contrast and high resolution images because a radiologist must be able to distinguish between tissues having relatively small differences in X-ray absorption rates.

Scattered X-ray radiation (sometimes referred to as secondary or off-axis radiation) is a problem in X-ray imaging. Scattered radiation causes a loss of image contrast. Scattered X-ray radiation is a particularly serious problem in the field of mammography where high image contrast is necessary for the detection of very subtle changes in breast tissue. Scattered or secondary radiation can be caused by many sources, even the object under radiographic examination. In mammography, scatter is typically reduced by scatter reducing grids which only permit primary or on-axis radiation to reach the image receiver. However, particularly in mammography, despite using scatter reducing grids, it is important to reduce the potential for scatter radiation by limiting the size of the X-ray beam. This is typically accomplished through collimation.

A mammography apparatus is typically used to take both magnified and unmagnified mammographic images, and full field and spot images. Even with the range of views typically used, the prior art devices only employ two preset beam collimations, one for full field and the other for spot images. Although spot imaging can be either magnified or unmagnified, the prior art devices do not collimate the beam differently for either spot imaging technique. Instead, an arbitrary spot collimation setting is used.

Whether a breast is undergoing magnified or unmagnified spot imaging, or full field of view imaging, the distance between the compression paddle and the breast support (either the image receiver or another breast supporting device) varies with the thickness of the breast under compression. Prior art devices do not collimate the beam differently for breasts of different thicknesses. Ordinarily, the collimation of the beam in the prior art apparatus is set for an arbitrary collimation setting which may be for an average breast thickness. However, if the apparatus is set up to collimate the X-ray beam for an average breast thickness, as done by the prior art mammography apparatus, the X-ray beam collimation will not be optimized for thin breasts nor thick breasts. At either extreme, image quality can be affected. For example, with a thin breast, the X-ray beam area at the compression paddle may be larger than the compression paddle area, which may be undesirable because it can cause additional X-ray scattering, reducing image contrast. With a thick breast, the X-ray beam area may be smaller than the compression paddle area which may result in less than optimal imaging area.

SUMMARY OF THE INVENTION

Accordingly, it is one object of the present invention to provide a mammography apparatus with optimum X-ray beam collimation.

It is another object to provide a mammography apparatus with an X-ray beam collimator that is automatically adjusted to provide an appropriately collimated X-ray beam for a breast of any thickness.

It is another object of the present invention to provide a mammography apparatus with an X-ray beam collimator that is automatically adjusted to provide an appropriately collimated X-ray beam for any magnification factor.

It is another object of the present invention to provide a mammography apparatus with an X-ray beam collimator that is automatically adjusted to provide an X-ray beam that is appropriately collimated for any magnification factor for a breast of any thickness using a compression paddle of any dimension.

This object is accomplished, at least in part, by providing a mammography apparatus comprising an X-ray source; an X-ray image receiver; a beam collimator with an adjustable aperture; a compression paddle of predetermined dimensions positionable between the X-ray source and the X-ray image receiver; and means for adjusting the aperture of the beam collimator in proportion to the distance between the compression paddle and the X-ray source and the dimensions of the compression paddle.

Other objects and advantages of the present invention will become apparent to those skilled in the art from the following derailed description read in conjunction with the attached drawings and claims appended hereto.

BRIEF DESCRIPTION OF THE DRAWINGS

The drawings, not drawn to scale, include:

FIGS. 5A through 8A are schematic diagrams illustrating beam collimation for several spot mammographic imaging positions ranging from unmagnified to highly magnified; and FIGS. 5B through 8B are schematic diagrams of the resulting image projected on the image receiving for the mammographic imaging positions of FIGS. 5A through 8A.

BEST MODE FOR CARRYING OUT THE INVENTION

Figure 1:
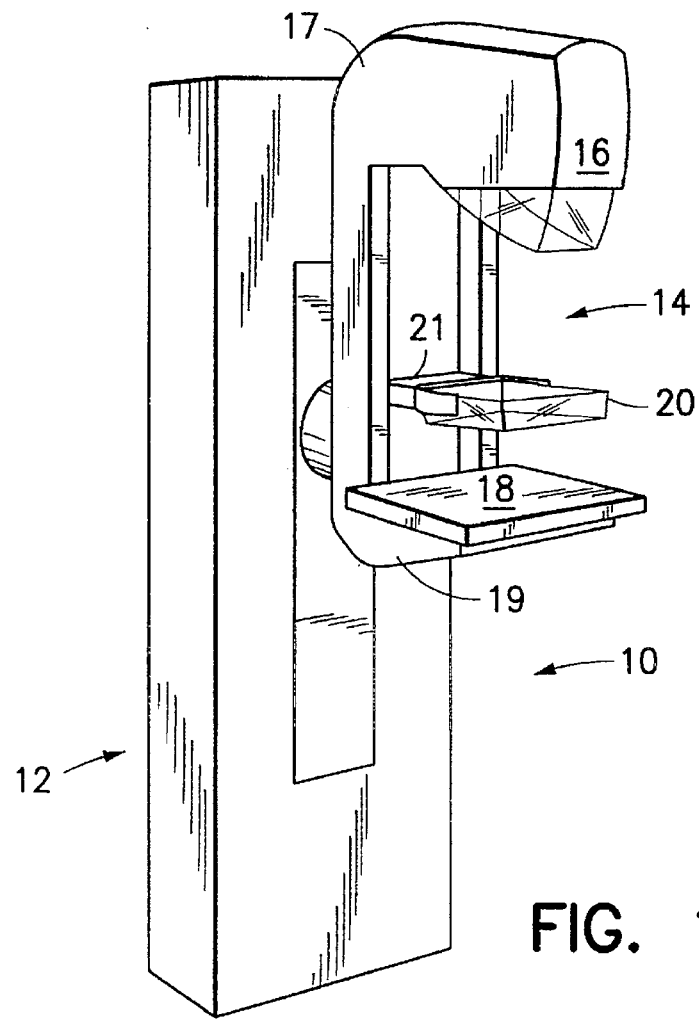
FIG. 1 is a perspective view of a mammography apparatus of the present invention.

FIG. 1 illustrates a mammography apparatus 10 which is similar, in some respects, to prior art apparatus used for mammographic imaging procedures. The apparatus of the present invention 10, generally comprises a base 12, an imaging arm 14 pivotally attached to the base 12, an X-ray tube 16 fixed to a first end 17 of the imaging arm 14, an image receiver 18 fixed at a second end 19 of the imaging arm 14. The apparatus 10 also includes a compression paddle holder 21 which is slidably attached to the imaging arm 14 and positioned between its first 17 and second 19 ends. A compression paddle 20 is held by the compression paddle holder 21.

Figure 2:
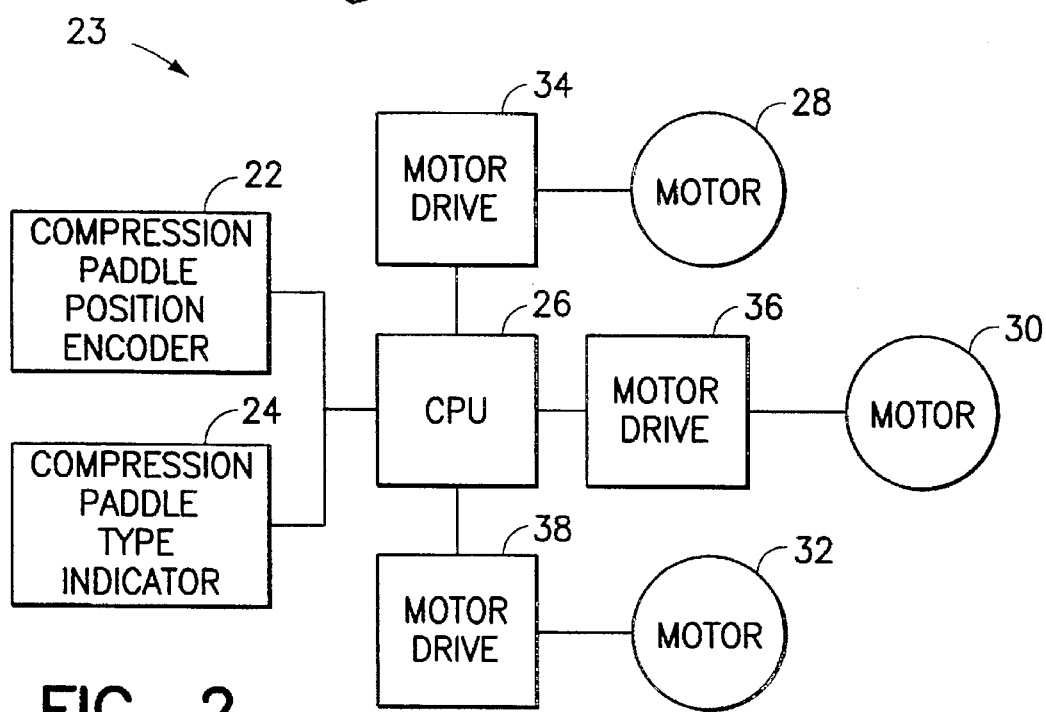
FIG. 2 is a block diagram of the controller system for automatically adjusting the aperture of the collimator.

With reference to FIG. 2, the present invention 10 differs from the prior art in that apparatus includes a collimator controller 23. The controller 23 comprises a position encoder 22 which is connected to the compression paddle holder 21 and a compression paddle type or dimension indicator 24 which indicates, via an optical encoder and look-up table, the compression paddle surface dimensions as indicated by symbolic information on the compression paddle. The indicator 24 is located on the compression paddle holder 21. The collimator controller 23 also comprises a central processing unit (CPU) 26 which is connected to the compression paddle position encoder 22 and compression paddle compression surface dimension indicator 24. The CPU 26 is connected so as to receive inputs from the position encoder 22 and dimension indicator 24. The CPU 26 is also connected to collimator blade motors 28, 30, and 32, through motor drive circuits 34, 36 and 38, respectively.

According to the present invention, the position encoder 22 provides information to the CPU 26 about the distance between the compression paddle 20, as held by the compression paddle holder 21, and the focal spot of the X-ray tube 16 to the CPU 26. The dimension indicator 24 provides information to the CPU 26 regarding the dimensions or area of the compression surface of a particular compression paddle 20 being used. Based on information received from the position encoder 22 and dimension indicator 24, the CPU 26 drives collimator blades in a forward or reverse direction via motors 28, 30, and 32 through motor drive circuits 34, 36 and 38 respectively.

Figure 3A:
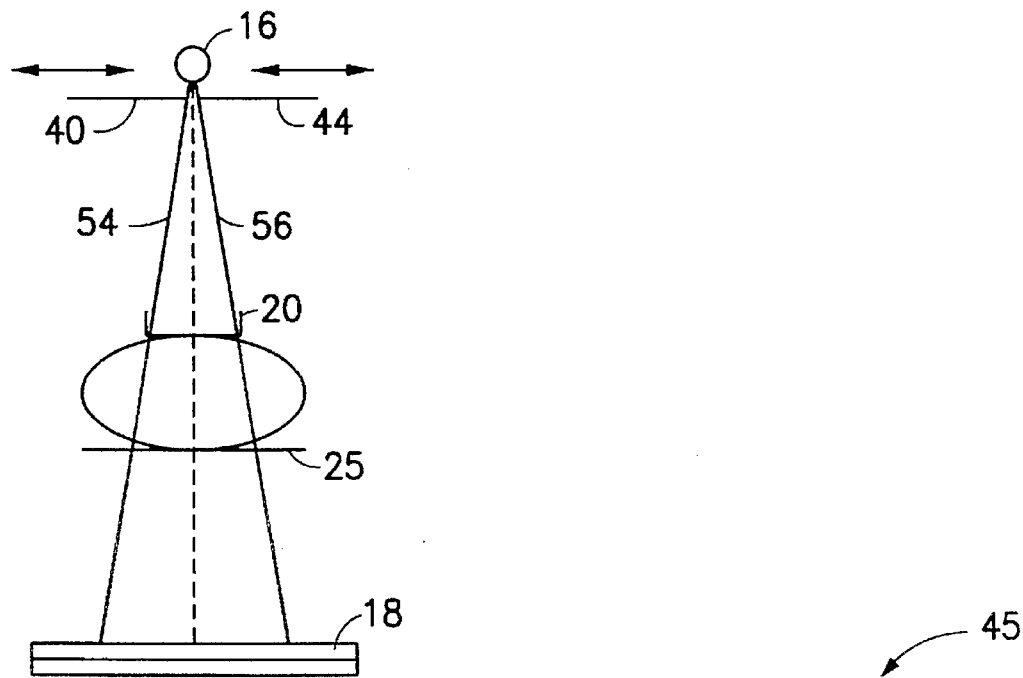
FIGS. 3A, 3B and 3C are schematic diagrams illustrating a spot mammography imaging position employing magnification for a thick breast, the collimator positioning for performing such mammographic imaging, and the resulting image projected on the image receiver.
Figure 3B:
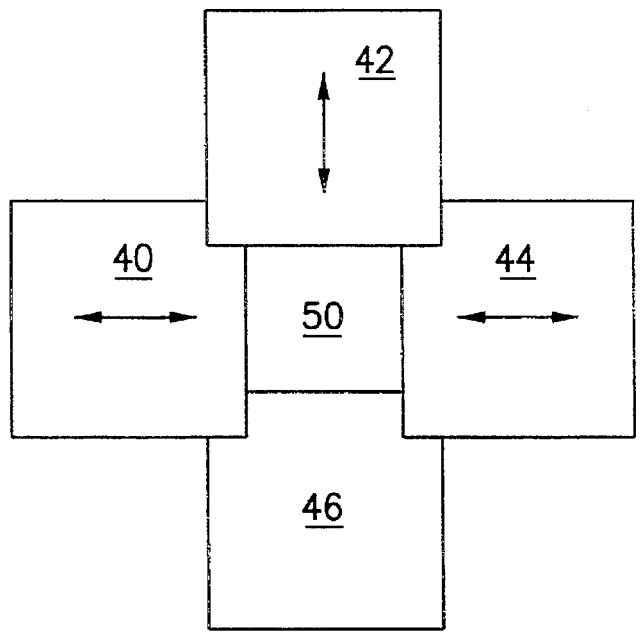
Figure 3C:
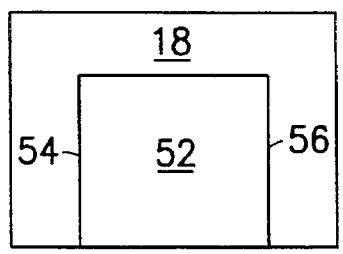
Figure 4A:
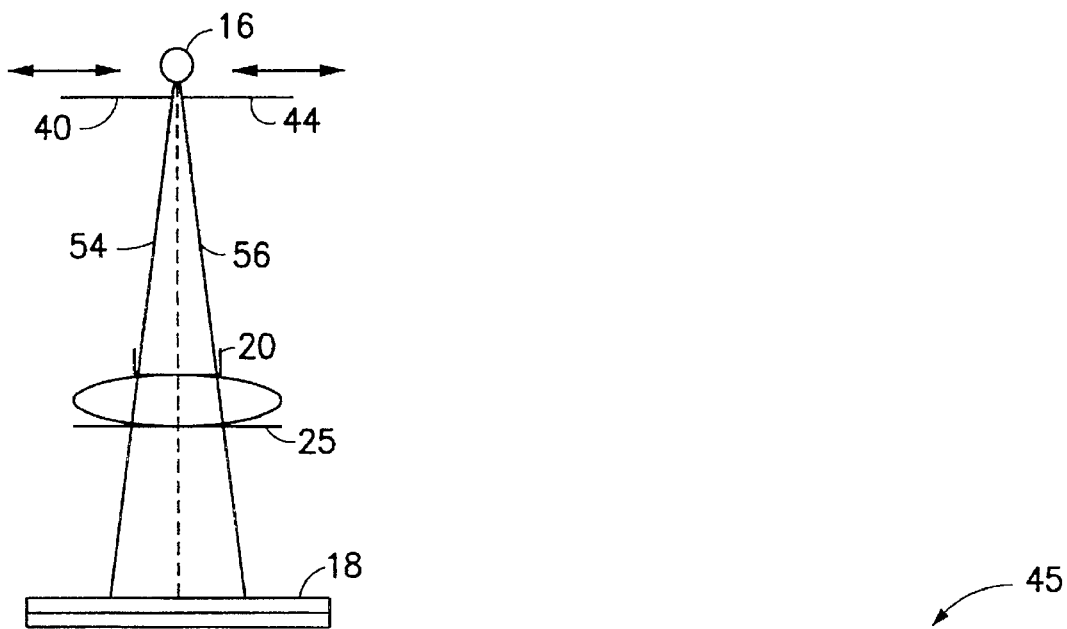
FIGS. 4A, 4B and 4C are schematic diagrams illustrating a spot mammographic imaging position employing the same magnification for a thin breast, the collimator positioning for performing such mammographic imaging, and the resulting image projected on the image receiver.
Figure 4B:
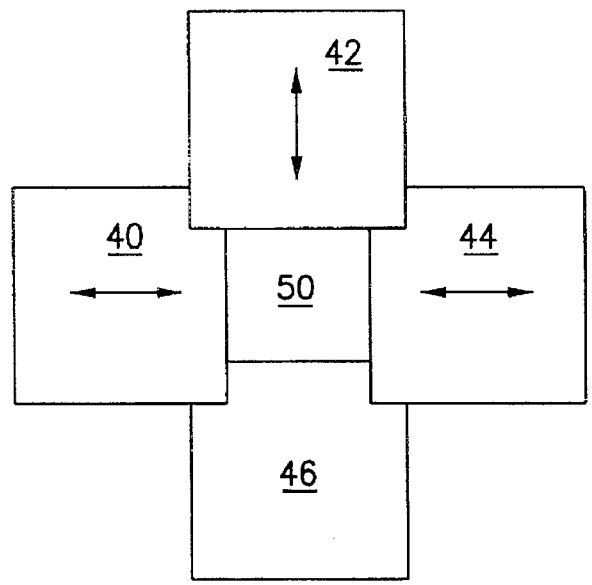
Figure 4C:
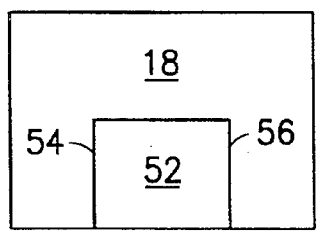

FIGS. 3A through 3C and 4A through 4C illustrate collimation of the X-ray beam by the present invention when spot imaging a thick breast and a thin breast, both at the same magnification factor as predetermined by the position of support plate 25. More specifically, comparing FIGS. 3A and 4A, compression paddle 20 in FIG. 4A is further from the X-ray source when imaging a thin breast than it is when imaging a thick breast as shown in FIG. 3A. Therefore, when imaging a thin breast at the same magnification, the X-ray beam must be made narrower so that outer most edges 54 and 56 project up to but not beyond the width of the compression paddle 20. Referring to FIGS. 3B and 4B, based upon compression paddle position as determined by information from encoder 22 and based upon dimension indicator 24, overlapping collimator blades 40, 42, and 44 of collimator 45 are driven inwardly (FIG. 4B), by motors 28, 30, and 32, as compared to their respective positions when imaging a thick breast (FIG. 3B). The amount of movement is determined by CPU 26. Collimator blade 46 usually remains stationary as that edge is typically fixed to guide the beam along the patient's chest wall. As compared with the size of the aperture 50 of the collimator 45 for thick breast imaging, the aperture 50 of the collimator 45 is made smaller to collimate the X-ray beam more narrowly when imaging a thin breast. FIGS. 3C and 4C illustrate the resulting projected magnified image 52 of a thick and thin breast, respectively, on image receiver 18.

The precise beam collimation provided by the present invention provides the advantage of maximizing image area while reducing potential scatter from X-rays impinging on areas not of interest. For example, if the beam collimation were not precisely controlled, but rather set to an arbitrary middle point between the thick and thin breast imaging, then in the case of imaging a thick breast, the beam edges 54 and 56 would not extend to the edges of the compression paddle 20 resulting in an image that may be less than a desired maximum size. In the case of imaging a thin breast, the beam edges 54 and 56 would likely exceed the edges compression paddle 20 and potentially cause increased X-ray scattering because X-rays would impinge on areas that are outside the area of interest, which is ordinarily only the tissue under the compression paddle 20.

Prior art mammography apparatus ordinarily provides for only two beam collimation settings, one for a predetermined spot view, either magnified or unmagnified and the other for a full field view. With only two preset beam collimation settings, the prior art mammography apparatus are not capable of automatically providing optimized beam collimation for a range of magnification factors, such as those shown in FIGS. 6A, 7A, or 8A. If optimal beam collimation is desired, a manual means for adjusting collimation must be used which results in longer setup times and variability in the results. If optimal collimation is not used, than if collimation for unmagnified spot imaging (FIG. 5A) is used as the preset collimation setting, then the imaging area in all magnified spot images (FIGS. 6A, 7A and 8A) will be less than optimal. On the other hand, if collimation is preset for maximum magnified spot imaging (FIG. 8A), such as that shown in FIG. 8A, then the edges 54 and 56 of the beam will exceed the compression paddle 20 width in all lesser magnification factor views (FIGS. 5A, 6A and 7A) and, as compared to the, present invention, an increase in X-ray scattering can be expected as X-rays impinge upon areas outside the area of interest. Alternatively, if the collimation is preset for a position between the unmagnified (FIG. 5A) and maximum magnification (FIG. 8A) then images taken at the unmagnified spot and maximum magnification spot will not be taken with optimal collimation.

However, unlike the prior art, a virtual infinite range of breast thicknesses can be imaged under virtually an infinite number of magnification factors with optimal beam collimation for each magnification factor and thickness through the proportionally controlled collimation of the present invention. Optimal beam collimation is accomplished with the present invention, as described above, using knowledge of the compression paddle dimensions and compression paddle position. FIGS. 5B through 8B illustrate the image 52 projected on image receiver 18 from the mammography techniques illustrated in FIGS. 5A through 8A, respectively. These images illustrate the difference in the size of the projected image 52 through proportional beam collimation with the present invention.

It will thus be seen that the objects and advantages set forth above and those made apparent from the preceding descriptions, are efficiently attained and, since certain changes may be made in the above construction without departing from the scope of the invention, it is intended that the matter contained in the above description or shown in the accompanying drawings shall be interpreted as illustrative and not in a limiting sense. It is also to be understood that the following claims are intended to cover all of the genetic and specific features of the invention herein described, and all statements of the scope of the invention which, as a matter of language, might be said to fall therebetween.

What is claimed is:

1. A mammography apparatus comprising:

an X-ray source;

an X-ray image receiver positioned to receive X-rays from the X-ray source;

means for compressing tissue, the means being positionable between the X-ray source and the X-ray image receiver and wherein the means further providing a compression surface of predetermined dimensions;

a beam collimator positioned between the X-ray source and the means for compressing tissue, the collimator forming an adjustable aperture;

first indicating means for providing a signal proportional to the distance between the means for compressing tissue and the X-ray source;

second indicating means for providing a signal proportional to the size of the compression paddle surface;

means, responsive to the first and second indicating means, for determining the size of the aperture of the beam collimator in proportion to the indicated distance between the means for compressing tissue and the X-ray source and in proportion to the indicated size of the compression surface of predetermined dimensions; and means, responsive to the determining means, for adjusting the size of the beam collimator's aperture.

2. The apparatus of claim 1, wherein the means for determining the size of the aperture comprises a central processing unit having an input adapted to receive the signals from the first and second indicating means and wherein the central processing unit further includes an output for providing an output signal to the means for adjusting the aperture.

3. The apparatus of claim 2, wherein the beam collimator further comprises a plurality of position adjustable collimator blades.

4. The apparatus of claim 3, wherein the aperture adjusting means comprises at least one motor.

5. The apparatus of claim 3, wherein the aperture adjusting means comprises a plurality of motors.

6. A mammography apparatus comprising:

an imaging arm having a first end and a second end;

an X-ray source attached to the first end of the imaging arm;

an X-ray image receiver positioned at the second end of the imaging arm to receive X-rays from the X-ray source;

a compression paddle holder slidably attached to the imaging arm between its first end and its second end;

a position encoder connected to the compression paddle holder;

a compression paddle compression surface dimension indicator connected to the compression paddle holder;

a compression paddle of predetermined dimensions attached to the compression paddle holder, the compression paddle having means for indicating its dimensions to the compression paddle dimension indicator;

a beam collimator forming an aperture positioned between the X-ray source and the compression paddle holder, the collimator further including means for adjusting the size of the aperture; and a collimator controller comprising a central processing unit adapted to receive input from the position encoder and the compression paddle dimension indicator, and further adapted to provide output, based on input received from the encoder and indicator, to the means for adjusting the size of the aperture of the beam collimator.

7. A mammography apparatus comprising:

an imaging arm having a first end and a second end;

an X-ray source attached to the first end of the imaging arm;

an X-ray image receiver positioned at the second end of the imaging arm to receive X-rays from the X-ray source;

a compression paddle holder slidably attached to the imaging arm between its first end and its second end;

a position encoder connected to the compression paddle holder;

a compression paddle dimension indicator connected to the compression paddle holder;

a compression paddle having a compression surface of predetermined dimensions attached to the compression paddle holder, the compression paddle having means for indicating its compression surface dimensions to the compression paddle dimension indicator;

an X-ray beam collimator positioned between the X-ray source and the compression paddle holder, the collimator comprising a plurality of movable blades forming an aperture;

means for moving the plurality of movable blades to adjust the size the aperture; and a collimator controller comprising a central processing unit adapted to receive input from the position encoder and the compression paddle dimension indicator, and further adapted to provide output, based on input received from the encoder and indicator, to means for moving the plurality of movable collimator blades.

* * * * *